United States Patent
Liu et al.

(10) Patent No.: US 12,145,957 B2
(45) Date of Patent: *Nov. 19, 2024

(54) PREPARATION METHOD FOR GLUFOSINATE

(71) Applicant: LIER CHEMICAL CO., LTD., Sichuan (CN)

(72) Inventors: Yongjiang Liu, Sichuan (CN); Lei Zhou, Sichuan (CN); Wei Zeng, Sichuan (CN); Min Xu, Sichuan (CN); Ke Cheng, Sichuan (CN)

(73) Assignee: LIER CHEMICAL CO., LTD., Mianyang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/303,613

(22) Filed: Apr. 20, 2023

(65) Prior Publication Data

US 2023/0331750 A1 Oct. 19, 2023

Related U.S. Application Data

(63) Continuation of application No. PCT/CN2022/106398, filed on Jul. 19, 2022.

(30) Foreign Application Priority Data

Jul. 20, 2021 (CN) .......................... 202110817019.5

(51) Int. Cl.
| | |
|---|---|
| *C07F 9/54* | (2006.01) |
| *C07C 237/06* | (2006.01) |
| *C07C 323/32* | (2006.01) |
| *C07C 323/59* | (2006.01) |

(52) U.S. Cl.
CPC .......... *C07F 9/5407* (2013.01); *C07C 237/06* (2013.01); *C07C 323/32* (2013.01); *C07C 323/59* (2013.01)

(58) Field of Classification Search
CPC ........ C07F 9/32; C07F 9/5407; C07C 237/06; C07C 323/02; C07C 323/59; C07C 323/32
See application file for complete search history.

(56) References Cited

U.S. PATENT DOCUMENTS

| | | | |
|---|---|---|---|
| 5,442,088 A | 8/1995 | Hoffmann | |
| 5,900,237 A | 5/1999 | Napper et al. | |
| 11,680,077 B2 * | 6/2023 | Liu | ........................ C07F 9/4866 562/11 |
| 11,897,907 B2 * | 2/2024 | Xu | ........................ C07F 9/4006 |

FOREIGN PATENT DOCUMENTS

| | | | | |
|---|---|---|---|---|
| CN | 106083922 | * | 11/2016 | ................ C07F 9/30 |
| CN | 109232644 | | 1/2019 | |
| GB | 1596884 | | 9/1981 | |
| JP | 2014520101 | | 8/2014 | |
| KR | 20200087620 | | 7/2020 | |
| WO | 2020145513 | | 7/2020 | |
| WO | 2020145514 | | 7/2020 | |
| WO | 2020145627 | | 7/2020 | |
| WO | WO 2021147894 | * | 7/2021 | ................ C07F 9/30 |

OTHER PUBLICATIONS

CN106083922, Shandong Acad of Pesticide Sciences: Shandong Kexin Biochemical Co Ltd, Refined glufosinate preparation method, English translation, 15 pages (Year: 2016).*

Hoffmann, M. G. et al., "A Novel and Convenient Route to L-Homoserine Lactones and L-Phosphinothricin From L-Aspartic Acid", Tetrahedron Letters, vol. 33, No. 19, Dec. 31, 1992 (Dec. 31, 1992), pp. 2669-2672.

Bayer VE, Gugel KH, Hägele K, Hagenmaier H, Jessipow S, Koenig WA, Zähner H. Phosphinothricin und phosphinothricyl-alanyl-alanin. Helv. Chim. Acta. 1972;55(224). [Machine Translation of Abstract].

* cited by examiner

*Primary Examiner* — Yate' K Cutliff

(74) *Attorney, Agent, or Firm* — Robin L. Teskin; Baker, Donelson, Bearman, Caldwell & Berkowitz PC

(57) ABSTRACT

A preparation method for glufosinate or a salt, an enantiomer or a mixture of enantiomers in all ratios thereof, the method being especially suitable for the preparation of glufosinate, and greatly shortening steps in an existing preparation process. Especially in the preparation of L-glufosinate, the product can effectively retain the ee value of the raw materials.

30 Claims, No Drawings

PREPARATION METHOD FOR GLUFOSINATE

CROSS-REFERENCE TO RELATED APPLICATIONS

This application is a continuation application of Int'l Appl. No. PCT/CN2022/106398, filed Jul. 19, 2022, which claims priority to Chinese Appl. No. 202110817019.5 filed Jul. 20, 2021, each and all of which are incorporated herein by reference in their entireties.

FIELD OF THE INVENTION

The present invention relates to a preparation method for glufosinate.

BACKGROUND OF THE INVENTION

Glufosinate is an important herbicide.

SUMMARY OF THE INVENTION

The present invention provides a method for preparing glufosinate of formula (I) or a salt, an enantiomer thereof or a mixture of the enantiomers in all ratios, comprising the following steps:

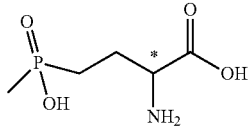

(I)

a) reacting a compound of formula (II) or a salt, an enantiomer thereof or a mixture of the enantiomers in all ratios,

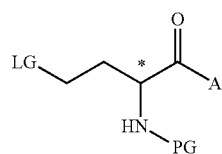

(II)

with one or more compounds of formula (III) or a mixture;
the above mixture being a mixture comprising one or more compounds of formula (IV) and one or more compounds of formula (V); or a mixture comprising one or more compounds of formula (IV) and one or more compounds of formula (III); or a mixture comprising one or more compounds of formula (V) and one or more compounds of formula (III); or a mixture comprising one or more compounds of formula (III), one or more compounds of formula (IV) and one or more compounds of formula (V);

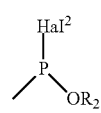

(III)

(IV)

(V)

b) reacting the intermediate, no matter whether it is isolated or not, in the presence of water and an acid or a base to obtain the glufosinate (I) or a salt, an enantiomer thereof or a mixture of the enantiomers in all ratios;

wherein when PG is an amino protecting group, a step of removing the amino protecting group can be further comprised;

wherein: LG is $Hal^1$, —OTs or $Hal^1$

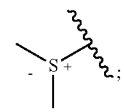

$Hal^1$ and $Hal^2$ are each independently halogen, e.g., fluorine, chlorine, bromine or iodine;

PG is hydrogen or an amino protecting group, and the amino protecting group preferably is —C(=O)R, —C(=O)OR or —S(=O)$_2$R;

A is —$NHR_1$, —$NR_1R_{1'}$ or —$OR_1$;

R, $R_1$, $R_{1'}$, $R_2$, $R_3$ and $R_4$ are each independently selected from the group consisting of $C_1$-$C_6$ alkyl, $C_{3-10}$ cycloalkyl, $C_{6-10}$ aryl, $C_{6-12}$ aralkyl, 5- to 14-membered heteroaryl and 3- to 10-membered heterocyclyl, and when the mixture comprises the mixture of one or more compounds of formula (IV) and one or more compounds of formula (III), or when the mixture comprises the mixture of one or more compounds of formula (III), one or more compounds of formula (IV) and one or more compounds of formula (V), $R_2$ is either $R_3$ or $R_4$;

the chiral carbon atom is labeled with *; and provided that at least one of the following conditions is met:

1) the compound of formula (II) is not

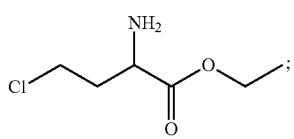

2) the compound of formula (III) is not

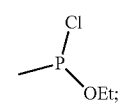

3) the compound of formula (IV) is not

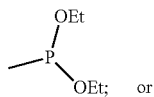

or 4) the compound of formula (V) is not

The present invention further provides a method for preparing enantiomerically pure glufosinate of formula (I) or a salt thereof,

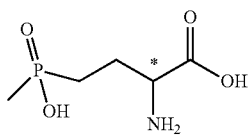
(I)

the method comprises the following steps:
a1) reacting an enantiomerically pure compound of formula (II) or a salt thereof,

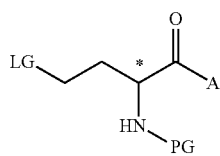
(II)

with a compound of formula (III),

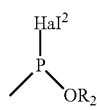
(III)

or one or more compounds of formula (III) or a mixture; the above mixture being a mixture comprising one or more compounds of formula (IV) and one or more compounds of formula (V); or a mixture comprising one or more compounds of formula (IV) and one or more compounds of formula (III); or a mixture comprising one or more compounds of formula (V) and one or more compounds of formula (III); or a mixture comprising one or more compounds of formula (III), one or more compounds of formula (IV) and one or more compounds of formula (V);

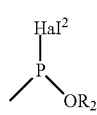
(III)

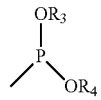
(IV)

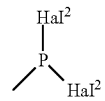
(V)

b1) reacting the intermediate, no matter whether it is isolated or not, in the presence of water and an acid or a base to obtain the enantiomerically pure glufosinate (I) or a salt thereof;
wherein when PG is an amino protecting group, a step of removing the amino protecting group can be further comprised;
wherein
LG is $Hal^1$, —OTs or $Ha^1$

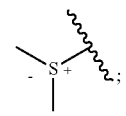

$Hal^1$ and $Hal^2$ are each independently halogen, e.g., fluorine, chlorine, bromine or iodine;
PG is hydrogen or an amino protecting group, and the amino protecting group preferably is —C(=O)R, —C(=O)OR or —S(=O)$_2$R;
A is —NHR$_1$, —NR$_1$R$_{1'}$ or —OR$_1$;
R, R$_1$, R$_{1'}$, R$_2$, R$_3$ and R$_4$ are each independently selected from the group consisting of $C_1$-$C_6$ alkyl, $C_{3-10}$ cycloalkyl, $C_{6-10}$ aryl, $C_{6-12}$ aralkyl, 5- to 14-membered heteroaryl and 3- to 10-membered heterocyclyl, and when the mixture comprises the mixture of one or more compounds of formula (IV) and one or more compounds of formula (III), or when the mixture comprises the mixture of one or more compounds of formula (III), one or more compounds of formula (IV) and one or more compounds of formula (V), R$_2$ is either R$_3$ or R$_4$;
the chiral carbon atom is labeled with *;
provided that at least one of the following conditions is met:
1) the compound of formula (II) is not

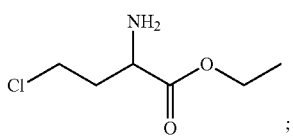

2) the compound of formula (III) is not

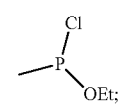

3) the compound of formula (IV) is not

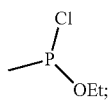

or 4) the compound of formula (V) is not

In certain specific embodiments, one compound of formula (III) is employed.

In certain specific embodiments, a mixture of one compound of formula (IV) and one compound of formula (V) is employed, and the mixture can be further added with a compound of formula (III) in any ratio.

Further, the enantiomeric ratio is (L):(D)-enantiomer or (D):(L)-enantiomer of 50.5:49.5 to 99.5:0.5.

Further, the enantiomeric ratio is (L):(D)-enantiomer of 50.5:49.5 to 99.5:0.5.

In some embodiments, R is $C_1$-$C_6$ alkyl or $C_{6-10}$ aryl, preferably is methyl, ethyl, tert-butyl, phenyl or p-methylphenyl.

In some embodiments, said PG is hydrogen, —C(=O)CH$_3$, —C(=O)Ph, —C(=O)OC$_2$H$_5$, —C(=O)OC(CH$_3$)$_3$ or

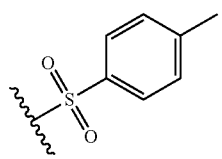

In some embodiments, said Hal$^1$ is chlorine, bromine or iodine.

In some embodiments, LG is chlorine, bromine, iodine, —OTs or

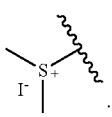

In some embodiments, said Hal$^2$ is chlorine.

In some embodiments, said $R_1$, $R_{1'}$, $R_2$, $R_3$ and $R_4$ are each independently $C_1$-$C_6$ alkyl or $C_{6-12}$ aralkyl, preferably are $C_1$-$C_4$ alkyl or benzyl.

In some embodiments, said $R_1$ and $R_{1'}$ are each independently methyl, ethyl, n-propyl, isopropyl, n-butyl, isobutyl or benzyl.

In some embodiments, A is —NHCH$_2$CH$_2$CH$_2$CH$_3$, —N(CH$_3$)$_2$, —OCH$_3$, —OCH$_2$CH$_3$, —OCH$_2$CH$_2$CH$_3$, —OCH(CH$_3$)$_2$, —OCH$_2$CH$_2$CH$_2$CH$_3$, —OCH$_2$CH(CH$_3$)$_2$ or —OBn.

In some embodiments, said $R_2$ is methyl, ethyl, n-propyl, isopropyl, n-butyl or isobutyl, preferably is n-propyl, isopropyl or n-butyl.

In some embodiments, said $R_3$ is methyl, ethyl, n-propyl, isopropyl, n-butyl or isobutyl, preferably is n-propyl, isopropyl or n-butyl.

In some embodiments, said $R_4$ is methyl, ethyl, n-propyl, isopropyl, n-butyl or isobutyl, preferably is n-propyl, isopropyl or n-butyl.

In certain specific embodiments, the mixture is a mixture of one or more compounds of formula (IV) and one or more compounds of formula (III), and the molar ratio of the compounds of formula (IV) to the compounds of formula (III) is (0.9-1.1):1 or (0.05-1.1):1; or the mixture is a mixture of one or more compounds of formula (V) and one or more compounds of formula (III), and the molar ratio of the compounds of formula (V) to the compounds of formula (III) is (0.9-1.1):1 or (0.05-1.1):1; or the mixture is a mixture comprising one or more compounds of formula (IV) and one or more compounds of formula (V), and the molar ratio of the compounds of formula (IV) to the compounds of formula (V) is (0.9-1.1):1.

Further, in aforementioned step a) or a1), the reaction can proceed at room temperature, the reaction temperature can be 20-200° C., and preferably 90-140° C. in consideration of reaction efficiency.

Further, the aforementioned step a) or a1) is carried out in the presence of a base.

Further, the base in aforementioned step a) or a1) is an organic base or ammonia.

Further, in aforementioned step a) or a1), the organic base is selected from the group consisting of an organic amine, pyridine or a pyridine derivative having 1-3 substituents attached to one or more carbon atoms in the heterocycle, piperidine or a piperidine derivative having 1-3 substituents attached to one or more carbon atoms in the heterocycle.

Further, the organic base is selected from the group consisting of triethylamine, piperidine or pyridine.

Further, in aforementioned step a) or a1), the molar ratio of the base to the total amounts of the compound of formula (III) and the compound of formula (V) is (1-10):1.

Further, in aforementioned step a) or a1), the reaction is carried out under a solvent-free condition or in an inert solvent.

Further, in aforementioned step a) or a1), the inert solvent is selected from any one or more of benzene solvents, amide solvents, hydrocarbon solvents, halogenated hydrocarbon solvents, sulfone or sulfoxide solvents, ether solvents or ester solvents; preferably, the inert solvent is selected from any one or more of benzene solvents, amide solvents, halogenated hydrocarbon solvents, ether solvents or ester solvents.

Further, in aforementioned step a) or a1), the inert solvent is selected from any one or more of chlorobenzene, trimethylbenzene, 1,4-dioxane, 1,2-dichloroethane, dimethyl sulfoxide, N-methylpyrrolidone, N,N-dimethylformamide, petroleum ether, n-heptane, tetrahydrofuran, methyltetrahydrofuran, benzene, toluene, ethyl acetate, and butyl acetate.

Further, in aforementioned step a) or a1), the molar ratio of the compound of formula (III) or the mixture to the compound of formula (II) is 1:(0.8-10), preferably 1:(1-3); or the molar ratio of the compound of formula (II) to the compound of formula (III) or the mixture is 1:(0.8-10), preferably 1:(1-3).

Further, the total reaction time of aforementioned step a) or a1) is 0.5 hour to 25 hours, preferably 1 hour to 20 hours or 1 hour to 15 hours, most preferably 1 hour to 5 hours.

Further, in aforementioned step b) or b1), an inorganic acid or an organic acid is added.

Further, the inorganic acid is hydrochloric acid or sulfuric acid.

Further, in aforementioned step b) or b1), the base is an inorganic base or an organic base.

Further, the base is alkali metal hydroxide, alkali-earth metal hydroxide, alkali metal carbonate, alkali-earth metal carbonate, alkali metal bicarbonate or alkali-earth metal bicarbonate.

Further, the base is NaOH, KOH or Ba(OH)$_2$.

Further, in aforementioned step b) or b1), the reaction temperature is 20-150° C.

In some embodiments, the present disclosure provides a compound of formula (II) or a salt thereof,

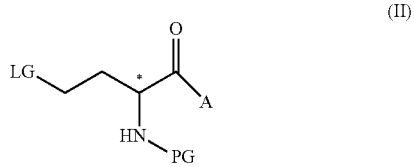

wherein the compound of formula (II) is selected from the group consisting of:

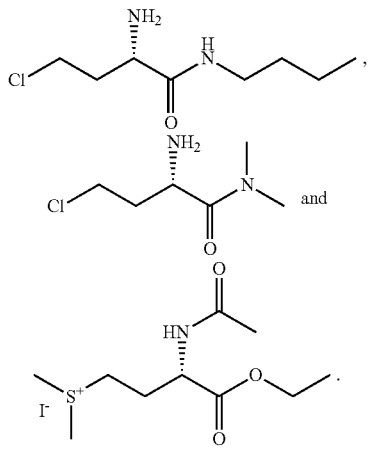

In some embodiments, the present disclosure provides use of the aforementioned compound in the preparation of glufosinate or a salt thereof, or L-glufosinate or a salt thereof.

The method of the present invention is particularly suitable for the preparation of glufosinate, and substantially reduces the steps of the existing preparation processes. In particular, in the preparation of L-glufosinate, the product can effectively maintain the ee value of the raw material. For example, when an enantiomerically pure raw material (e.g., the enantiomeric excess percentage (% ee) is greater than 90%) is employed, the enantiomeric excess percentage (% ee) of the prepared L-glufosinate is greater than e.g., 50%, 55%, 60%, 65%, 70%, 75%, 80%, 85%, 90% or 95%.

Unless otherwise specified, the terms used in the specification and claims have the following meanings.

The term "amino protecting group" refers to a group that can be attached to a nitrogen atom in an amino group to protect the amino group from participating the reaction and can be easily removed in the subsequent reactions. Suitable amino protecting groups include, but are not limited to, the following protecting groups:

carbamate group of formula —C(=O)O—R$^a$, wherein R$^a$ is e.g., methyl, ethyl, tert-butyl, benzyl, phenethyl, CH$_2$=CH—CH$_2$—, etc.; amide group of formula —C(=O)—R$^b$, wherein R$^b$ is methyl, ethyl, phenyl, trifluoromethyl, etc.; N-sulfonyl derivative group of formula —S(=O)$_2$—R$^c$, wherein R$^c$ is e.g., tolyl, phenyl, trifluoromethyl, 2,2,5,7,8-pentamethylchroman-6-yl-, 2,3,6-trimethyl-4-methoxybenzene, etc.

The term "alkyl" refers to a saturated aliphatic hydrocarbon group, including linear and branched groups having 1 to 18 carbon atoms. Alkyl having 1 to 6 carbon atoms (i.e., $C_1$-$C_6$ alkyl), such as methyl, ethyl, propyl, 2-propyl, n-butyl, isobutyl, tert-butyl and pentyl, is preferred. The alkyl can be substituted or unsubstituted, and when substituted, the substituent can be halogen, nitro, sulfonyl, ether oxy, ether thio, ester, thioester or cyano.

The $C_1$-$C_4$ alkyl is linear or branched, comprising saturated hydrocarbon chain having 1 to 4 carbon atoms. It can be methyl, ethyl, propyl, isopropyl, butyl, isobutyl, sec-butyl or tert-butyl.

As used herein, the term "cycloalkyl" refers to a saturated monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0]nonyl, decahydronaphthalene, etc.)), which is optionally substituted with one or more (e.g., 1 to 3) suitable substituents. The cycloalkyl has 3 to 15 carbon atoms. For example, the term "$C_{3-10}$ cycloalkyl" refers to a saturated monocyclic or polycyclic (e.g., bicyclic) hydrocarbon ring having 3 to 10 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the term "heterocyclyl" refers to a saturated or unsaturated, monovalent, monocyclic or bicyclic residue having 2, 3, 4, 5, 6, 7, 8 or 9 carbon atoms and one or more (e.g., 1, 2, 3 or 4) heteroatom-containing groups selected from the group consisting of C(=O), O, S, S(=O), S(=O)$_2$, and NR$^d$ wherein R$^d$ represents a hydrogen atom, $C_{1-6}$ alkyl, or $C_{1-6}$ haloalkyl group, in the ring. A heterocyclyl may be linked to the rest of a molecule through any one of the carbon atoms or a nitrogen atom (if present). In particular, 3- to 10-membered heterocyclyl refers to a group having 3 to 10 carbon atoms and heteroatom(s) in the ring, such as, but are not limited to, oxiranyl, aziridinyl, azetidinyl, oxetanyl, tetrahydrofuranyl, dioxolinyl, pyrrolidinyl, pyrrolidinonyl, imidazolidinyl, pyrazolidinyl, pyrrolinyl, tetrahydropyranyl, piperidinyl, morpholinyl, dithianyl, thiomorpholinyl, piperazinyl or trithianyl.

As used herein, the term "aryl" refers to an all-carbon monocyclic or fused-ring polycyclic aromatic group having a conjugated π electron system. For example, as used herein, the term "$C_{6-10}$ aryl" refers to an aromatic group containing 6 to 10 carbon atoms, such as phenyl or naphthyl. Aryl is optionally substituted with one or more (such as 1 to 3) suitable substituents (e.g., halogen, —OH, —CN, —NO$_2$, $C_{1-6}$ alkyl).

The term "aralkyl" preferably means aryl substituted alkyl, wherein aryl and alkyl are as defined herein. Normally, the aryl group may have 6-10 carbon atoms, and the alkyl group may have 1-6 carbon atoms. Exemplary aralkyl group includes, but is not limited to, benzyl, phenylethyl, phenylpropyl, phenylbutyl.

As used herein, the term "heteroaryl" refers to a monovalent monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same or different. Moreover, in each case, it can be benzo-fused. In particular, heteroaryl is selected from the group consisting of thienyl, furyl, pyrrolyl, oxazolyl, thiazolyl, imidazolyl, pyrazolyl, isoxazolyl, isothiazolyl, oxadiazolyl, triazolyl, thiadiazolyl etc., and benzo derivatives thereof; or pyridinyl, pyridazinyl, pyrimidinyl, pyrazinyl, triazinyl, etc., and benzo derivatives thereof.

The "mixture of the enantiomers in all ratios" as used herein has the same meaning as the "mixture of the enantiomers in any ratio".

DETAILED DESCRIPTION OF THE INVENTION

Example 1a: General Preparation Method for Compounds 1-5

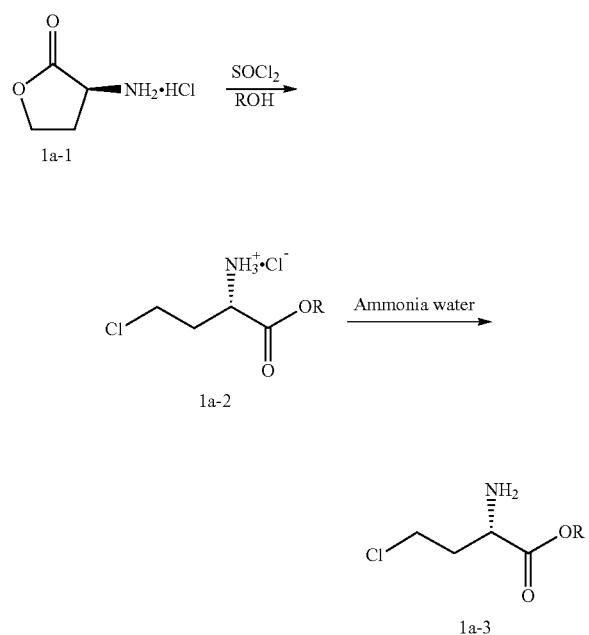

L-homoserine lactone hydrochloride (1a-1) (ee value of 99%, 0.1 mol) was added to a round bottom flask, and alcohol (the molar ratio of homoserine lactone hydrochloride to alcohol was about 1:(10~15)) was added. The temperature of the system was lowered to 10° C., and thionyl chloride (0.3 mol) was slowly dropwise added. The system temperature was maintained at 10° C., and stirred for 30 min. The temperature was gradually raised to 35° C., and the reaction was stirred for 20 hours, during which bubbles were continuously generated. The reaction was monitored by LC-MS or LC, until the reaction was complete (for complete reaction of certain substrates, raising reaction temperature was necessary). The temperature of the system was lowered to room temperature, the remaining thionyl chloride and solvent were distilled off under reduced pressure, the solid residue was slurried with 100 mL of a mixed solvent of n-hexane and ethyl acetate (the volume ratio of n-hexane to ethyl acetate was 2:1), and the filter cake was obtained through filtration. The wet product 1a-2 was neutralized with ammonia water, the system was adjusted to pH 7-8, and extracted with ethyl acetate. The organic phase was collected, dried and concentrated to obtain the target product compound 1a-3.

Example 1b: Preparation of Compound 16

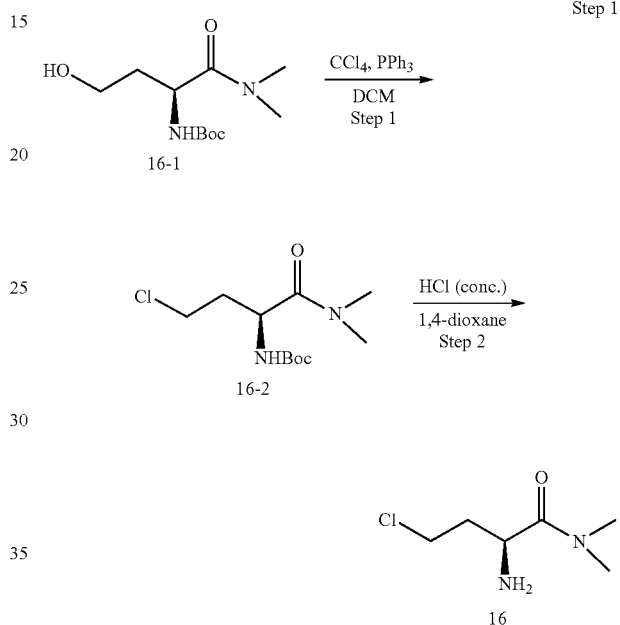

The synthesis was conducted using compound 16-1 as the starting material (the synthesis described in Weitz, Iris S. et al., Journal of Organic Chemistry (1997), 62(8), 2527-2534, can be referred to). At room temperature, compound 16-1 (40 mmol), DCM (20 ml), carbon tetrachloride (20 ml) and triphenylphosphine (120 mmol) were added to a round bottom flask, and then stirred at room temperature for 2 hours. TLC indicated that the raw materials underwent a complete reaction, and compound 16-2 was obtained by column chromatography at a yield of 50%.

MS (ESI): m/z [M+H]$^+$ calculated for $C_{11}H_{22}ClN_2O_3$: 265.13; found: 265.1.

$^1$H NMR (400 MHz, CDCl$_3$) δ 4.84 (td, J=8.8, 4.0 Hz, 1H), 3.80-3.44 (m, 2H), 3.12 (s, 3H), 2.97 (s, 3H), 2.16-2.03 (m, 1H), 1.96 (ddt, J=14.5, 8.9, 5.6 Hz, 1H), 1.43 (s, 9H).

Step 2

Compound 16-2 (20 mmol) was added to a round bottom flask, followed by addition of 1,4-dioxane (60 ml) and 36% HCl (16 ml), and the reaction was stirred at room temperature overnight. The reaction solution was concentrated, and then ammonia water was added for neutralization, with the pH being adjusted to 7-8. The mixture was extracted with ethyl acetate, dried and concentrated to obtain compound 16.

Homoserine analogues in the following table were prepared by the methods of Example 1a, Example 1b or similar methods known in the art.

| No. | Homoserine analogue | Brief description of the preparation method | Characterization data |
|---|---|---|---|
| 1. | (structure: Cl-CH2CH2-CH(NH2)-C(O)-O-CH3) | The alcohol in Example 1a was replaced with methanol. | MS (ESI): m/z [M + H]$^+$ calculated for $C_5H_{11}ClNO_2$: 152.05; found: 152.1.<br>$^1$H NMR (400 MHZ, CDCl$_3$) δ 3.74-3.55 (m, 6H), 2.47 (s, 2H), 2.19-2.09 (m, 1H), 1.96-1.82 (m, 1H). |
| 2. | (structure: Cl-CH2CH2-CH(NH2)-C(O)-O-n-propyl) | The alcohol in Example 1a was replaced with n-propanol. | MS (ESI): m/z [M + H]$^+$ calculated for $C_7H_{15}ClNO_2$: 180.08; found: 180.1.<br>$^1$H NMR (400 MHZ, CDCl$_3$) δ 3.98 (tt, J = 7.1, 3.6 Hz, 2H), 3.69-3.49 (m, 3H), 2.10 (ddt, J = 14.1, 8.3, 5.6 Hz, 1H), 1.82 (ddt, J = 14.5, 9.0, 5.6 Hz, 1H), 1.73 (s, 2H), 1.61-1.52 (m, 2H), 0.85 (t, J = 7.4 Hz, 3H). |
| 3. | (structure: Cl-CH2CH2-CH(NH2)-C(O)-O-iPr) | The alcohol in Example 1a was replaced with isopropanol. | MS (ESI): m/z [M + H]$^+$ calculated for $C_7H_{15}ClNO_2$: 180.08; found: 180.1.<br>$^1$H NMR (400 MHZ, DMSO-d$_6$) δ 4.91 (td, J = 6.3, 1.6 Hz, 1H), 3.81-3.62 (m, 2H), 3.39 (dt, J = 9.3, 3.6 Hz, 1H), 2.05-1.93 (m, 1H), 1.93-1.70 (m, 3H), 1.20 (t, J = 5.7 Hz, 6H).<br>$^{13}$C NMR (100 MHZ, DMSO-d$_6$) δ 174.7, 67.5, 51.5, 42.1, 37.04, 21.5. |
| 4. | (structure: Cl-CH2CH2-CH(NH2)-C(O)-O-n-butyl) | The alcohol in Example 1a was replaced with n-butanol. | MS (ESI): m/z [M + H]$^+$ calculated for $C_8H_{17}ClNO_2$: 194.10; found: 194.1.<br>$^1$H NMR (400 MHZ, CDCl$_3$) δ 4.05 (tt, J = 6.7, 3.4 Hz, 2H), 3.72-3.49 (m, 3H), 2.20-2.07 (m, 1H), 1.95 (s, 2H), 1.85 (ddt, J = 14.4, 8.9, 5.6 Hz, 1H), 1.61-1.51 (m, 2H), 1.31 (h, J = 7.6 Hz, 2H), 0.86 (q, J = 6.9 Hz, 3H). |
| 5. | (structure: Cl-CH2CH2-CH(NH2)-C(O)-O-isobutyl) | The alcohol in Example 1a was replaced with isobutanol. | MS (ESI): m/z [M + H]$^+$ calculated for $C_8H_{17}ClNO_2$: 194.10; found: 194.1.<br>$^1$H NMR (400 MHZ, DMSO-d$_6$) δ 3.92-3.65 (m, 4H), 3.48 (dd, J = 9.1, 4.5 Hz, 1H), 2.16-1.73 (m, 5H), 0.90 (d, J = 6.8 Hz, 6H).<br>$^{13}$C NMR (100 MHZ, DMSO-d$_6$) δ 175.1, 70.0, 51.5, 42.1, 37.1, 27.3, 18.8. |
| 6. | (structure: Cl-CH2CH2-CH(NH2)-C(O)-O-CH2-phenyl) | It was prepared according to a method similar to that disclosed in WO 2006117552 A1. | — |
| 7. | (structure: Br-CH2CH2-CH(NH2)-C(O)-O-Et) | It was prepared according to a method disclosed in WO 98/58256. | — |
| 8. | (structure: (CH3)2S$^+$-CH2CH2-CH(NHAc)-C(O)-O-Et, I$^-$) | It was prepared according to a method similar to that disclosed in Journal of Organic Chemistry (2007), 72(21), 8046-8053. | MS (ESI): m/z M$^+$ calculated for $C_{10}H_{20}NO_3S^+$: 234.12; found: 234.1<br>$^1$H NMR (400 MHZ, DMSO-d$_6$) δ 8.36 (dd, J = 8.1, 2.8 Hz, 1H), 4.35 (dddd, J = 10.5, 7.7, 4.7, 2.4 Hz, 1H), 4.10 (qd, J = 7.1, 2.1 Hz, 2H), 3.36 (ddt, J = 11.9, 5.8, 2.9 Hz, 2H), 2.95 (dd, J = 4.5, 2.6 Hz, 6H), 2.28-2.11 (m, 1H), 2.11-1.95 (m, 1H), 1.87 (d, J = 1.3 Hz, 3H), 1.18 (td, J = 7.1, 2.1 Hz, 3H).<br>$^{13}$C NMR (100 MHZ, DMSO-d$_6$) δ 170.7, 169.7, 61.0, 50.6, 25.2, 24.4, 22.5, 14.0. |
| 9. | (structure: Cl-CH2CH2-CH(NHBz)-C(O)-O-Et) | It was prepared according to a method similar to that disclosed in CN 110386882 A. | MS (ESI): m/z [M + H]$^+$ calculated for $C_{13}H_{17}ClNO_3$: 270.09; found: 270.1.<br>$^1$H NMR (400 MHZ, DMSO-d$_6$) δ 8.80 (d, J = 7.6 Hz, 1H), 8.01-7.76 (m, 2H), 7.60-7.53 (m, 1H), 7.49 (t, J = 7.3 Hz, 2H), 4.61 (ddd, J = 9.6, 7.6, 5.0 Hz, 1H), 4.13 (qd, J = 7.1, 1.8 Hz, 2H), 3.89-3.62 (m, 2H), 2.36-2.13 (m, 2H), 1.19 (t, J = 7.1 Hz, 3H).<br>$^{13}$C NMR (100 MHZ, DMSO-d$_6$) δ 171.5, 166.8, 133.6, 131.6, 128.3, 127.5, 60.8, 50.3, 41.9, 33.3, 14.1. |

| No. | Homoserine analogue | Brief description of the preparation method | Characterization data |
|---|---|---|---|
| 10. | (structure: ethyl ester with CN group and N-sulfonyl-phenyl) | It was prepared according to a method similar to that disclosed in CN 110386882 A. | MS (ESI): m/z [M + H]$^+$ calculated for C$_{13}$H$_{19}$ClNO$_4$S: 320.07; found: 320.1.<br>$^1$H NMR (400 MHZ, DMSO-d$_6$) δ 8.32 (d, J = 9.0 Hz, 1H), 7.64 (dd, J = 8.2, 1.6 Hz, 2H), 7.44-7.30 (m, 2H), 3.95 (tdd, J = 8.9, 6.3, 2.2 Hz, 1H), 3.85 (q, J = 7.1 Hz, 2H), 3.59 (dt, J = 11.3, 5.7 Hz, 1H), 3.51 (ddd, J = 11.0, 8.1, 5.7 Hz, 1H), 2.43-2.25 (m, 3H), 1.97 (ttd, J = 14.3, 10.4, 9.2, 7.4 Hz, 2H), 1.02 (t, J = 7.1 Hz, 3H).<br>$^{13}$C NMR (101 MHZ, DMSO-d$_6$) δ 170.6, 142.7, 138.1, 129.4, 126.5, 60.9, 53.0, 41.0, 34.8, 20.9, 13.7. |
| 11. | (structure: N-acetyl ethyl ester with Cl) | It was prepared according to a method disclosed in WO 2020/145514 A1. | MS (ESI): m/z [M + H]$^+$ calculated for C$_8$H$_{15}$ClNO$_3$: 208.08; found: 208.1.<br>$^1$H NMR (400 MHZ, DMSO-d$_6$) δ 8.31 (d, J = 7.7 Hz, 1H), 4.37 (ddd, J = 9.4, 7.6, 4.9 Hz, 1H), 4.09 (qd, J = 7.1, 1.8 Hz, 2H), 3.83-3.44 (m, 2H), 2.08 (dddd, J = 20.1, 14.4, 8.2, 4.2 Hz, 2H), 1.86 (s, 3H), 1.18 (t, J = 7.1 Hz, 3H).<br>$^{13}$C NMR (100 MHZ, DMSO-d$_6$) δ 171.6, 169.6, 60.7, 49.6, 41.5, 33.7, 22.3, 14.0. |
| 12. | (structure: Cl with methoxyacetyl amide ethyl ester) | It was prepared according to a method disclosed in CN 110386882 A | MS (ESI): m/z [M + H]+ calculated for C$_9$H$_{17}$ClNO$_4$: 238.09; found: 238.1.<br>$^1$H NMR (400 MHZ, DMSO-d$_6$) δ 7.60 (d, J = 8.0 Hz, 1H), 4.14 (dddt, J = 27.3, 9.5, 7.1, 3.7 Hz, 3H), 4.00 (q, J = 7.1 Hz, 2H), 3.82-3.46 (m, 2H), 2.08 (ddt, J = 13.1, 8.9, 4.7 Hz, 2H), 1.18 (q, J = 6.9 Hz, 6H). |
| 13. | (structure: Cl with N-Boc ethyl ester) | It was prepared according to a method reported in J. Med. Chem. 1994, 37, 2950-2957. | MS (ESI): m/z [M + H]$^+$ calculated for C$_{11}$H$_{21}$ClNO$_4$: 266.12; found: 266.2.<br>$^1$H NMR (400 MHZ, DMSO-d$_6$) δ 7.33 (d, J = 8.0 Hz, 1H), 4.53-3.93 (m, 3H), 3.65 (tdd, J = 14.7, 11.0, 6.2 Hz, 2H), 2.36-1.90 (m, 2H), 1.38 (s, 9H), 1.18 (td, J = 7.1, 3.1 Hz, 3H).<br>$^{13}$C NMR (100 MHZ, DMSO-d$_6$) δ 172.0, 155.6, 78.4, 60.6, 51.1, 41.7, 33.4, 28.1, 14.0. |
| 14. | (structure: NH$_2$, Cl, N-isopropyl amide) | Compound 16-1 in Example 1b was replaced with (structure: HO, NHBoc, N-isopropyl amide). | MS (ESI): m/z [M + H]$^+$ calculated for C$_7$H$_{16}$ClN$_2$O: 179.10; found: 179.1.<br>$^1$H NMR (400 MHZ, D$_2$O) δ 4.06 (t, J = 6.9 Hz, 1H), 3.93 (p, J = 6.6 Hz, 1H), 3.78-3.54 (m, 2H), 2.31 (qd, J = 6.7, 2.0 Hz, 2H), 1.13 (dd, J = 6.6, 2.4 Hz, 6H).<br>$^{13}$C NMR (100 MHZ, D$_2$O) δ 167.5, 51.3, 42.3, 39.7, 33.4, 21.2, 21.1. |
| 15. | (structure: NH$_2$, Cl, N-butyl amide) | Compound 16-1 in Example 1b was replaced with (structure: HO, NHBoc, N-butyl amide). | MS (ESI): m/z [M + H]$^+$ calculated for C$_8$H$_{18}$ClN$_2$O: 193.11; found: 193.1.<br>$^1$H NMR (400 MHZ, D$_2$O) δ 4.18 (t, J = 6.9 Hz, 1H), 3.79-3.65 (m, 2H), 3.33 (dt, J = 13.8, 7.0 Hz, 1H), 3.22 (dt, J = 13.6, 6.9 Hz, 1H), 2.42-2.31 (m, 2H), 1.59-1.49 (m, 2H), 1.41-1.26 (m, 2H), 0.91 (t, J = 7.4 Hz, 3H).<br>$^{13}$C NMR (100 MHZ, D$_2$O) δ 168.5, 51.4, 39.8, 39.5, 33.5, 30.2, 19.4, 13.0. |
| 16. | (structure: NH$_2$, Cl, N,N-dimethyl amide) | See Example 1b | MS (ESI): m/z [M + H]$^+$ calculated for C$_6$H$_{14}$ClN$_2$O: 165.08; found: 165.1.<br>$^1$H NMR (400 MHZ, D$_2$O) δ 4.65 (dd, J = 7.7, 4.8 Hz, 1H), 3.79-3.64 (m, 2H), 3.09 (s, 3H), 2.93 (s, 3H), 2.30 (dddd, J = 13.7, 11.2, 7.7, 3.9 Hz, 2H).<br>$^{13}$C NMR (100 MHZ, D$_2$O) δ 168.5, 48.6, 39.8, 37.1, 35.9, 32.6. |

| No. | Homoserine analogue | Brief description of the preparation method | Characterization data |
|---|---|---|---|
| 17. | (structure: TsO-CH2CH2-CH(NHAc)-C(O)OEt) | It was prepare according to a method similar to that disclosed in Journal of Organic Chemistry (1986), 51(26), 5047-50. | MS (ESI): m/z [M + H]$^+$ calculated for C$_{15}$H$_{22}$NO$_6$S: 344.40; found: 344.4.<br>$^1$H NMR (400 MHZ, CDCl$_3$) δ 7.93-7.49 (m, 2H), 7.36-7.17 (m, 2H), 5.85 (d, J = 9.1 Hz, 1H), 4.24-4.06 (m, 2H), 4.06-3.92 (m, 3H), 2.41 (s, 3H), 2.14-2.03 (m, 1H), 2.00 (s, 4H), 1.11 (t, J = 7.1 Hz, 3H).<br>$^{13}$C NMR (100 MHZ, CDCl$_3$) δ 171.1, 170.6, 143.5, 136.6, 129.5, 127.1, 61.7, 59.8, 52.8, 31.8, 21.3, 20.6, 13.7. |

Example 2

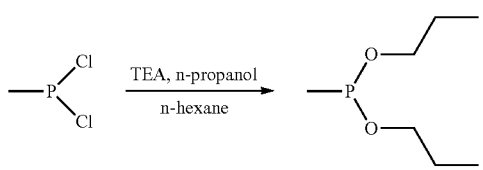

At −10° C., n-propanol (0.9 mol), triethylamine (0.9 mol) and n-hexane (450 ml) were added to a round bottom flask, and dichloro(methyl)phosphane (0.45 mol) was added dropwise through a constant-pressure dropping funnel for about 1 hour. The reaction was warmed to 0° C., and allowed to proceed for 2 hours for complete reaction. The mixture was filtered, the solid was washed with n-hexane (150 ml×2), and the mother liquor was evaporated under reduced pressure to remove the solvent. Dipropyl methylphosphonite (colorless liquid, yield: 86%, content: 94%) was obtained through fractionation (the fractionation temperature is not higher than 60° C.).

MS (ESI): m/z [M+H]$^+$ calculated for C$_7$H$_{18}$O$_2$P: 165.11; found: 165.1.

$^1$H NMR (400 MHz, CDCl$_3$) δ 3.65 (ddddt, J=10.0, 6.2, 5.0, 3.5, 1.7 Hz, 4H), 1.51 (q, J=7.1 Hz, 4H), 1.12 (dd, J=8.3, 1.2 Hz, 3H), 0.82 (td, J=7.4, 1.1 Hz, 6H).

$^{13}$C NMR (100 MHz, CDCl$_3$) δ 68.2, 24.6, 19.9, 10.2.

$^{31}$P NMR (160 MHz, CDCl$_3$) δ 33.5.

The following compounds were prepared according to a method similar to that described above.

| No. | Alkyl phosphonite | Difference as compared with the method in Example 2 | Characterization data |
|---|---|---|---|
| 1 | (diisopropyl methylphosphonite structure) | n-propanol was replaced with isopropanol. | MS (ESI): m/z [M + H]$^+$ calculated for C$_7$H$_{18}$O$_2$P: 165.11; found: 165.1.<br>$^1$H NMR (400 MHz, CDCl$_3$) δ 4.11 (dp, J = 9.6, 6.2 Hz, 2H), 1.18-1.06 (m, 15H).<br>$^{13}$C NMR (100 MHz, CDCl$_3$) δ 70.3, 24.7, 21.5.<br>$^{31}$P NMR (160 MHz, CDCl$_3$) δ 30.1. |
| 2 | (dibutyl methylphosphonite structure) | n-propanol was replaced with n-butanol. | MS (ESI): m/z [M + H]$^+$ calculated for C$_9$H$_{22}$O$_2$P: 193.14; found: 193.1.<br>$^1$H NMR (400 MHz, CDCl$_3$) δ 3.70 (pd, J = 7.5, 7.1, 3.3 Hz, 4H), 1.53-1.43 (m, 4H), 1.35-1.22 (m, 4H), 1.15-1.07 (m, 3H), 0.83 (qd, J = 7.3, 6.8, 3.3 Hz, 6H).<br>$^{13}$C NMR (100 MHz, CDCl$_3$) δ 66.3, 33.5, 20.0, 19.0, 13.7.<br>$^{31}$P NMR (160 MHz, CDCl$_3$) δ 28.7. |

Example 3

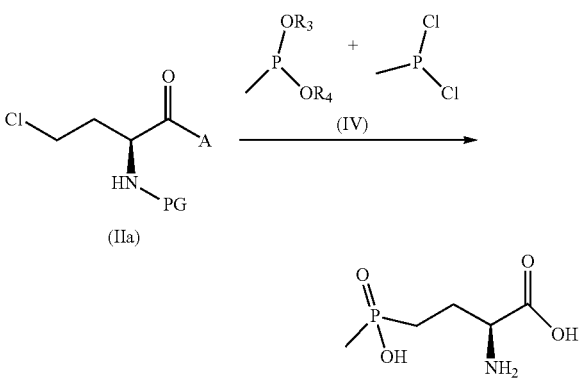

Under a nitrogen atmosphere, at −10° C., a solution of a compound of Formula (IV) (0.6 eq, 90% purity) in chlorobenzene was added to a round bottom flask, and a solution of dichloro(methyl)phosphane (0.6 eq, 98% purity) in chlorobenzene was added dropwise through a constant-pressure dropping funnel at a rate of 1 d/s. After the dropwise addition was complete, the reaction was stirred for 10 min (at this time, the corresponding compound of Formula (III)

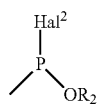
(III)

could be generated, wherein Hal² is chlorine, and R₂ is either R₃ or R₄). Subsequently, a solution of a compound of Formula (IIa) (1.0 eq) and triethylamine (1.2 eq, 98% purity) in chlorobenzene was added thereto at a rate of 4 d/s, and the stirring was continued for 30 min after the dropwise addition. The reaction was warmed to room temperature and stirred for 1h, and then the temperature was raised to 90° C., and the reaction was continued for 12h. The reaction was naturally cooled to room temperature, filtered with suction, and the filter cake was washed with chlorobenzene (150 mL×3). The filtrate was rotary evaporated to remove chlorobenzene, resulting in an intermediate. The intermediate was added with 100 mL concentrated hydrochloric acid (36%), heated to 90° C., and the reaction was allowed to proceed for 10h. MS detection indicated that the intermediate disappeared, the mixture was naturally cooled to room temperature, rotary evaporated to remove the solvent, and added with 95% ethanol (300 mL). The solution was heated to reflux until the crude product was completely dissolved, naturally cooled for crystallization, filtered and dried to obtain L-glufosinate hydrochloride.

According to the above method, L-glufosinate hydrochloride was prepared from the substrates in the table below. The reaction yield and ee value of the product are shown in the table below.

| No. | Compound of Formula (IIa) | Compound of Formula (IV) | Yield | ee value |
|---|---|---|---|---|
| 1. | ![structure] | ![structure] | 76% | 98% |
| 2. | ![structure] | | 78.2% | 98% |
| 3. | ![structure] | | 65.1% | 95% |
| 4. | ![structure] | | 79.7% | 98% |
| 5. | ![structure] | | 48.4% | 99% |
| 6. | ![structure] | | 24.8% | 65% |
| 7. | ![structure] | | 38% | 86% |

-continued

| No. | Compound of Formula (IIa) | Compound of Formula (IV) | Yield | ee value |
|---|---|---|---|---|
| 8. | *(ethyl N-acetyl-4-chloro-2-aminobutanoate structure)* | | 70.80% | 96% |
| 9. | *(ethyl N-ethoxycarbonyl-4-chloro-2-aminobutanoate structure)* | | 34.1% | 93% |
| 10. | *(ethyl N-tert-butoxycarbonyl-4-chloro-2-aminobutanoate structure)* | | 35% | 97% |
| 11. | *(4-chloro-2-amino-N-isopropylbutanamide structure)* | | 19.4% | 53% |
| 12. | *(4-chloro-2-amino-N-butylbutanamide structure)* | | 22% | 91% |
| 13. | *(4-chloro-2-amino-N,N-dimethylbutanamide structure)* | | 43% | 73% |
| 14. | *(ethyl 4-chloro-2-aminobutanoate structure)* | *(methyl dipropyl phosphonite structure)* | 82% | 97% |
| 15. | | *(methyl dibutyl phosphonite structure)* | 74.5% | 95% |

Example 4

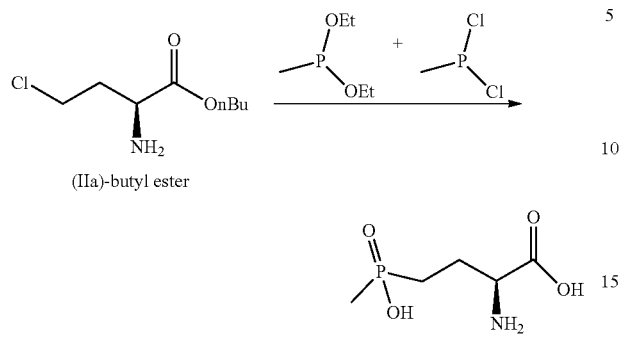

(IIa)-butyl ester

Under a nitrogen atmosphere, at −10° C., a solution of diethyl methylphosphonite (861.7 g, 0.55 eq, 90% purity) in chlorobenzene (6.0 kg) was added to a 20 L Jacketed Glass Reactor, and a solution of dichloro(methyl)phosphane (679.5 g, 0.55 eq, 98% purity) in chlorobenzene (2.0 kg) was added dropwise through a constant-pressure dropping funnel at a rate of 5 d/s. After the dropwise addition was complete, the reaction was stirred for 10 min (at this time, chloro (ethoxy)(methyl)phosphane

could be generated). Subsequently, a solution of the compound of Formula (IIa)-butly ester (2.0 kg, 1.0 eq) and triethylamine (1.2 kg, 1.1 eq, 98% purity) in chlorobenzene (8.0 kg) was added thereto at a rate of 10 d/s, and the stirring was continued for 30 min after the dropwise addition. The reaction was warmed to room temperature and stirred for 30 min, and then the temperature was raised to 90° C., and the reaction was continued for 2h. The reaction was naturally cooled to room temperature, filtered with suction, and the filter cake was washed with chlorobenzene (2.5 L×2). The filtrate was rotary evaporated to remove chlorobenzene, resulting in an intermediate. The intermediate was added with 4.2 kg 36% wt. hydrochloric acid, heated to 95° C., and the reaction was allowed to proceed for 10h, and at the same time, butanol generated was distilled off. MS detection indicated that the intermediate disappeared, the mixture was naturally cooled to room temperature, rotary evaporated to remove the solvent, and added with 95% ethanol (6 L). The solution was heated to reflux until the crude product was completely dissolved, naturally cooled for crystallization, filtered and dried to obtain L-glufosinate hydrochloride (white, yield 88%, ee value 98%).

In addition to those described herein, according to the foregoing description, various modifications to the present invention would be apparent to those skilled in the art. Such modifications are intended to fall within the scope of the appended claims. Each reference cited herein (including all patents, patent applications, journal articles, books and any other disclosures) are incorporated herein by reference in its entirety.

What is claimed is:

1. A method for preparing a glufosinate compound of formula (I), a salt thereof, an enantiomer thereof, or a mixture of enantiomers thereof, which enantiomers may be present in any ratio, wherein the method comprises the following steps:

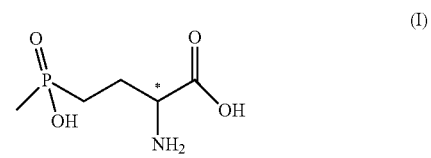

a) reacting a compound of formula (II) or a salt thereof, an enantiomer thereof or a mixture of enantiomers thereof, which enantiomers may be present in any ratio,

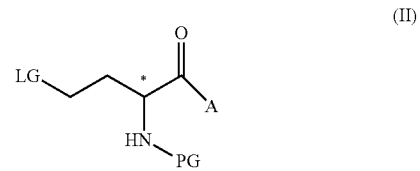

with one or more compounds of formula (III) or a mixture; wherein said mixture comprises one or more compounds of formula (IV) and one or more compounds of formula (V); or one or more compounds of formula (IV) and one or more compounds of formula (III); or one or more compounds of formula (V) and one or more compounds of formula (III); or one or more compounds of formula (III), one or more compounds of formula (IV), and one or more compounds of formula (V), wherein the reaction of a) results in a "reaction intermediate";

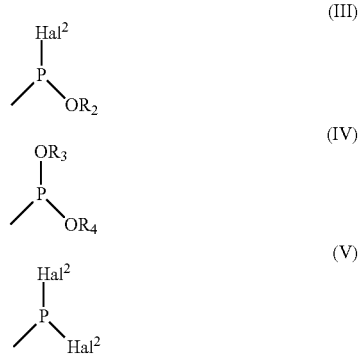

b) reacting the reaction intermediate which results from step a), wherein said reaction intermediate may or may not be in isolated form, with an acid or a base to obtain a glufosinate compound of formula (I) or a salt thereof, an enantiomer thereof, or a mixture of enantiomers thereof, which enantiomers may be present in any ratio;

wherein when PG is an amino protecting group, the method further optionally includes the removal of the amino protecting group;

further wherein:

LG is Hal$^1$, —OTs or Hal$^1$

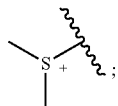

Hal$^1$ and Hal$^2$ are each independently halogen selected from fluorine, chlorine, bromine or iodine;

PG is hydrogen or an amino protecting group selected from —C(=O)R, —C(=O)OR and —S(=O)$_2$R;

A is —NHR$_1$, —NR$_1$R$_{1'}$, or —OR$_1$;

R, R$_1$, R$_{1'}$, R$_2$, R$_3$ and R$_4$ are each independently selected from the group consisting of C$_1$-C$_6$ alkyl, C$_{3-10}$ cycloalkyl, C$_{6-10}$ aryl, C$_{6-12}$ aralkyl, 5- to 14-membered heteroaryl and 3- to 10-membered heterocyclyl, with the further proviso that when the mixture comprises a mixture of one or more compounds of formula (IV) and one or more compounds of formula (III); or a mixture of one or more compounds of formula (III), one or more compounds of formula (IV) and one or more compounds of formula (V); then R$_2$ is either R$_3$ or R$_4$; and the chiral carbon atom is labeled with *; and with the further proviso that at least one of the following conditions is met:

1) the compound of formula (II) is not

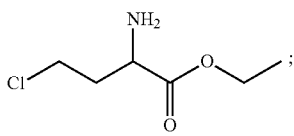

2) the compound of formula (III) is not

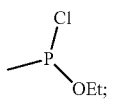

3) the compound of formula (IV) is not

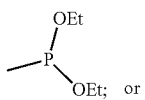

4) the compound of formula (V) is not

2. The method according to claim 1, wherein the glufosinate compound of formula (I) or salt thereof which results from the method is enantiomerically pure,

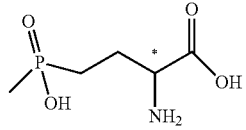

and wherein the compound of formula (II) in step a) is enantiomerically pure.

3. The method according to claim 1, wherein the enantiomeric ratio of (L):(D)-enantiomer or (D):(L)-enantiomer ranges from 50.5:49.5 to 99.5:0.5.

4. The method according to claim 1, wherein R is C$_{1-6}$ alkyl or C$_{6-10}$ aryl.

5. The method according to claim 1, wherein LG is chlorine, bromine, iodine, —OTs or

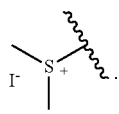

6. The method according to claim 1, wherein R$_1$, R$_{1'}$, R$_2$, R$_3$ and R$_4$ are each independently C$_1$-C$_6$ alkyl or C$_{6-12}$ aralkyl.

7. The method according to claim 1, wherein

R$_1$ and R$_{1'}$ are each independently methyl, ethyl, n-propyl, isopropyl, n-butyl, isobutyl or benzyl; or A is —NHCH$_2$CH$_2$CH$_2$CH$_3$, —N(CH$_3$)$_2$, —OCH$_3$, —OCH$_2$CH$_3$, —OCH$_2$CH$_2$CH$_3$, —OCH(CH$_3$)$_2$, —OCH$_2$CH$_2$CH$_2$CH$_3$, —OCH$_2$CH(CH$_3$)$_2$ or —OBn.

8. The method according to claim 1, wherein

R$_2$ is methyl, ethyl, n-propyl, isopropyl, n-butyl or isobutyl; or

R$_3$ is methyl, ethyl, n-propyl, isopropyl, n-butyl or isobutyl; or

R$_4$ is methyl, ethyl, n-propyl, isopropyl, n-butyl or isobutyl.

9. The method according to claim 1, wherein the mixture comprises one or more compounds of formula (IV) and one or more compounds of formula (III), and the molar ratio of the compounds of formula (IV) to the compounds of formula (III) ranges from 0.9:1 to 1.1:1 or 0.05:1 to 1.1:1; or the mixture comprises one or more compounds of formula (V) and one or more compounds of formula (III), and the molar ratio of the compounds of formula (V) to the compounds of formula (III) ranges from 0.9:1 to 1.1:1 or 0.05:1 to 1.1:1; or the mixture comprises one or more compounds of formula (IV) and one or more compounds of formula (V), and the molar ratio of the compounds of formula (IV) to the compounds of formula (V) ranges from 0.9:1 to 1.1:1.

10. The method according to claim 1, where in step a), the reaction temperature ranges from 20° C. to 200° C.

11. The method according to claim 1, where the reaction of step a) is conducted in the presence of a base.

12. The method according to claim 11, wherein the base in the reaction of step a) is an organic base selected from the group consisting of an organic amine, pyridine or a pyridine derivative having 1-3 substituents attached to one or more carbon atoms in the heterocycle, piperidine or a piperidine derivative having 1-3 substituents attached to one or more carbon atoms in the heterocycle or ammonia.

13. The method according to claim 12, wherein the organic base is selected from the group consisting of triethylamine, piperidine and pyridine.

14. The method according to claim 1, wherein in step a), the molar ratio of the base to the total amount of the compound of formula (III) and the compound of formula (V) ranges from 1:1 to 10:1.

15. The method according to claim 1, wherein in step a), the reaction is conducted under solvent-free conditions or in the presence of an inert solvent.

16. The method according to claim 15, wherein in step a), the inert solvent is selected from any one or more of benzene solvents, amide solvents, hydrocarbon solvents, halogenated hydrocarbon solvents, sulfone or sulfoxide solvents, ether solvents or ester solvents.

17. The method according to claim 15, wherein in step a), the inert solvent comprises one or more of chlorobenzene, trimethylbenzene, 1,4-dioxane, 1,2-dichloroethane, dimethyl sulfoxide, N-methylpyrrolidone, N,N-dimethylformamide, petroleum ether, n-heptane, tetrahydrofuran, methyltetrahydrofuran, benzene, toluene, ethyl acetate, and butyl acetate.

18. The method according to claim 1, wherein in step a), the molar ratio of the compound of formula (III) or the mixture to the compound of formula (II) ranges from 1:0.8 to 1:10; or the molar ratio of the compound of formula (II) to the compound of formula (III) or the mixture ranges from 1:0.8 to 1:10.

19. The method according to claim 1, wherein in step b), an inorganic acid or organic acid is added.

20. The method according to claim 19, wherein the inorganic acid is hydrochloric acid or sulfuric acid.

21. The method according to claim 1, wherein in step b), the base is an inorganic or organic base, wherein the inorganic base is selected from the group consisting of alkali metal hydroxide, alkali-earth metal hydroxide, alkali metal carbonate, alkali-earth metal carbonate, alkali metal bicarbonate and alkali-earth metal bicarbonate.

22. The method according to claim 21, wherein the base is NaOH, KOH or Ba(OH)$_2$.

23. The method according to claim 1, wherein in step b), the reaction temperature ranges from 20 to 150° C.

24. The method according to claim 1, wherein the compound of formula (II) is selected from the group consisting of:

| No. | The compound of formula (II) |
|---|---|
| 1. | |
| 2. | |
| 3. | |
| 4. | |
| 5. | |
| 6. | |
| 7. | |
| 8. | |
| 9. | |
| 10. | |
| 11. | |
| 12. | |

| No. | The compound of formula (II) |
|-----|------------------------------|
| 13. | 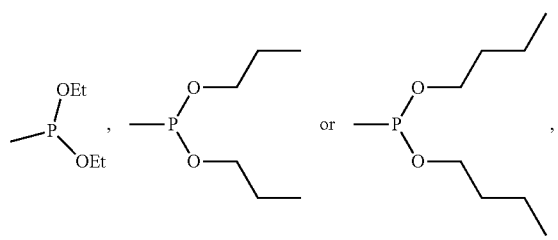 |
| 14. | | and/or,
the compound of formula IV is

and/or the compound of formula (V) is

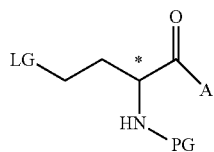

25. A compound of formula (II) or a salt thereof, (II)

wherein the compound of formula (II) is selected from the group consisting of:

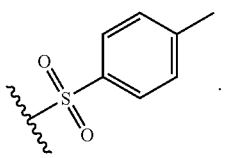 [SMILES: *S(=O)(=O)c1ccc(C)cc1]

26. The method according to claim 4, wherein R is methyl, ethyl, tert-butyl, phenyl or p-methylphenyl.

27. The method according to claim 1, wherein the PG is hydrogen, —C(=O)CH$_3$, —C(=O)Ph, —C(=O)OC$_2$H$_5$, —C(=O)OC(CH$_3$)$_3$ or

28. The method according to claim 6, wherein R$_1$, R$_{1'}$, R$_2$, R$_3$ and R$_4$ are each independently C$_1$-C$_4$ alkyl or benzyl.

29. The method according to claim 1, wherein in step a), the reaction temperature ranges from 90° C. to 140° C.

30. The method according to claim 1, wherein in step a), the molar ratio of the compound of formula (III) or the mixture to the compound of formula (II) ranges from 1:1 to 1:3; or the molar ratio of the compound of formula (II) to the compound of formula (III) or the mixture ranges from 1:1 to 1:3.

* * * * *

UNITED STATES PATENT AND TRADEMARK OFFICE
CERTIFICATE OF CORRECTION

PATENT NO. : 12,145,957 B2  
APPLICATION NO. : 18/303613  
DATED : November 19, 2024  
INVENTOR(S) : Yongjiang Liu et al.

Page 1 of 1

It is certified that error appears in the above-identified patent and that said Letters Patent is hereby corrected as shown below:

In the Claims

Claim 1, Column 23, Lines 2-9, delete:
LG is Hal¹, —OTs or Hal¹

"
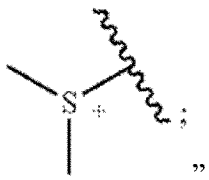
"

And insert:

LG is Hal¹, —OTs or

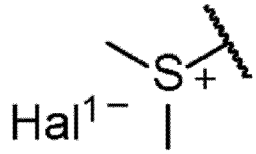

-- -- therefor.

Signed and Sealed this  
Sixteenth Day of September, 2025

Coke Morgan Stewart  
*Acting Director of the United States Patent and Trademark Office*